(12) United States Patent
Moeller

(10) Patent No.: US 12,044,674 B2
(45) Date of Patent: *Jul. 23, 2024

(54) METHOD AND SYSTEM FOR ASSESSING DRINKING BEHAVIOR

(71) Applicant: 1A Smart Start LLC, Grapevine, TX (US)

(72) Inventor: Michael Moeller, Newton, MA (US)

(73) Assignee: 1A Smart Start LLC, Grapevine, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 18/204,769

(22) Filed: Jun. 1, 2023

(65) Prior Publication Data

US 2024/0036030 A1 Feb. 1, 2024

Related U.S. Application Data

(63) Continuation of application No. 15/873,846, filed on Jan. 17, 2018, now Pat. No. 11,674,949.

(60) Provisional application No. 62/447,214, filed on Jan. 17, 2017.

(51) Int. Cl.
| | |
|---|---|
| *G01N 33/497* | (2006.01) |
| *A61B 5/00* | (2006.01) |
| *A61B 5/145* | (2006.01) |
| *A61B 5/1477* | (2006.01) |
| *G16H 10/20* | (2018.01) |
| *G16H 50/20* | (2018.01) |

(52) U.S. Cl.
CPC ........ *G01N 33/4972* (2013.01); *A61B 5/145* (2013.01); *A61B 5/1477* (2013.01); *A61B 5/4845* (2013.01); *G16H 10/20* (2018.01); *G16H 50/20* (2018.01); *A61B 5/7275* (2013.01); *A61B 2503/12* (2013.01)

(58) Field of Classification Search
None
See application file for complete search history.

(56) References Cited

U.S. PATENT DOCUMENTS

| | | | | |
|---|---|---|---|---|
| 5,944,661 | A * | 8/1999 | Swette | A61B 10/0064 600/362 |
| 8,010,663 | B2 * | 8/2011 | Firminger | G06F 16/24575 709/224 |
| 8,165,824 | B2 * | 4/2012 | Iiams | A61B 5/4266 600/300 |
| 2009/0182216 | A1 * | 7/2009 | Roushey, III | A61B 5/4266 600/364 |
| 2014/0210627 | A1 * | 7/2014 | Nothacker | G01N 33/4972 340/576 |

(Continued)

*Primary Examiner* — Michael R Bloch

(57) ABSTRACT

Method and system for self-assessment of drinking behavior. According to one embodiment, the method includes examining a transdermal alcohol response curve obtained from a drinking event, querying a user on their feelings of intoxication after or during the event, and using the combination of the objective measurement and subjective feelings of intoxication to provide an alert or status during subsequent drinking events. In so doing, the method mitigates at least some of the drawbacks associated with conventional alcohol monitoring devices by correlating an individual's reported feelings of intoxication with an objective transdermal measurement of alcohol.

20 Claims, 13 Drawing Sheets

(56) References Cited

U.S. PATENT DOCUMENTS

| | | | | |
|---|---|---|---|---|
| 2014/0365142 A1* | 12/2014 | Baldwin | .............. | A61B 5/0002 |
| | | | | 702/24 |
| 2015/0164416 A1* | 6/2015 | Nothacker | ............... | A61B 5/18 |
| | | | | 340/573.1 |
| 2016/0338627 A1* | 11/2016 | Lansdorp | ............... | A61B 5/681 |
| 2017/0086714 A1* | 3/2017 | Nothacker | ............. | A61B 5/681 |

* cited by examiner

METHOD AND SYSTEM FOR ASSESSING DRINKING BEHAVIOR

CROSS-REFERENCE TO RELATED APPLICATIONS

The present application is a continuation of U.S. patent application Ser. No. 15/873,846, inventor Michael Moeller, filed Jan. 17, 2018, which, in turn, claims the benefit under 35 U.S.C. 119(e) of U.S. Provisional Patent Application No. 62/447,214, inventor Michael Moeller, filed Jan. 17, 2017, the disclosures of both of which are incorporated herein by reference.

BACKGROUND OF THE INVENTION

The present invention relates generally to alcohol monitoring devices and relates more particularly to a new technique for assessing drinking behavior.

Alcohol monitoring devices, such as breathalyzers and wearable transdermal alcohol monitors, traditionally report alcohol measurements in terms of blood alcohol content (% BAC or BAC expressed in mg/dL). However, many physiological factors affect the blood alcohol concentration and a particular individual's feeling of intoxication, such as sex, body weight, body water, the consumption of food, medications, and an individual's alcohol metabolism and tolerance. Thus, an individual's subjective feeling of intoxication may vary with the same amount of alcohol when consumed at different times and under changing physiological conditions.

Since many alcohol monitoring devices do not measure the blood alcohol content directly in the liquid phase, these devices need a correlation factor between the alcohol measured in the vapor phase with the liquid concentration of alcohol contained in the blood. For instance, breathalyzers use a "partition coefficient" to correlate the deep-lung vapor phase alcohol being measured by the breathalyzer device that converts that measurement to % BAC (i.e., the liquid phase alcohol concentration in the blood). However, the average partition coefficient used by breathalyzers can vary by +/−30% or more. (See Hanson, D J, "Prevent unjust conviction for DWI or DUI charges," State University of New York—Potsdam, www2.potsdam.edu [Accessed Aug. 6, 2014]; and Jones, A W, "Quantitative measurements of the alcohol concentration and the temperature of breath during a prolonged exhalation," Acta Physiol Scand, 114(3), 407-412 (1982), both of which are incorporated herein by reference.) Similarly, wearable transdermal alcohol monitors use a correlation factor to relate the measured vapor phase alcohol diffusing through the skin to the liquid phase blood alcohol concentration. This correlation factor is also an average value that varies from individual-to-individual in a manner similar to the partition coefficient used with breathalyzers.

Therefore, due to the inherent physiological differences between individuals and the inherent variability in correlating a vapor phase alcohol measurement to a blood alcohol concentration, the reported % BAC provided by these measuring devices is often not the best gauge of an individual's subjective feelings of intoxication.

SUMMARY OF THE INVENTION

It is an object of the present invention to provide a method and system for assessing drinking behavior.

It is another object of the present invention to provide a method and system as described above that correlates an individual's subjective feelings about a drinking event with an objective transdermal measurement of alcohol during the same drinking event.

According to one aspect of the invention, there is provided a method for assessing drinking behavior to predict when alcohol consumption is likely to result in a subjective effect on the user, said method comprising the following steps: (a) using a transdermal alcohol sensor device to obtain a first transdermal alcohol measurement of a user for a first drinking event; (b) posing a query to the user about a subjective effect on the user of the first drinking event; (c) correlating a response of the user to the query about the subjective effect of the first drinking event with the first transdermal alcohol measurement of the user for the first drinking event to obtain a correlating factor; (d) during a second drinking event, using the transdermal alcohol sensor device to obtain a second transdermal alcohol measurement of the user; and (e) using the correlating factor and the second transdermal alcohol measurement to predict the subjective effect on the user from the second drinking event.

In another, more detailed feature of the invention, the subjective effect may be a subjective feeling of intoxication.

In another, more detailed feature of the invention, the posing step may be performed when a pre-determined blood alcohol level is measured by the transdermal alcohol sensor device.

In another, more detailed feature of the invention, the subjective effect may be a subjective feeling of being hungover.

According to another aspect of the invention, there is provided a method for assessing drinking behavior to predict when alcohol consumption is likely to result in a feeling of impairment or intoxication, said method comprising the following steps: (a) determining a peak blood alcohol (BAC) level of a user for a first drinking event, wherein the peak BAC level is detected using a transdermal alcohol sensor device; (b) querying the user about the user's subjective feelings of impairment or intoxication relating to the first drinking event; (c) correlating the user's subjective feelings of impairment or intoxication relating to the first drinking event to the peak BAC level from the first drinking event to establish a correlating factor; (d) monitoring the BAC level of the user during a second drinking event using the transdermal alcohol sensor device; and (e) providing a notification to the user, based on the BAC level of the user during the second drinking event and the correlating factor derived from the first drinking event, about potential for feelings of impairment or intoxication from the second drinking event.

In another, more detailed feature of the invention, the querying step may be performed after the BAC level of the user has returned to a baseline level.

In another, more detailed feature of the invention, the querying step may comprise providing the user with at least two options for a response.

In another, more detailed feature of the invention, the querying step may comprise providing the user with at least three options for a response.

In another, more detailed feature of the invention, the notification may comprise an alert on a user interface device that the BAC level for a feeling of impairment or intoxication has been reached or is on pace to be reached.

In another, more detailed feature of the invention, the notification may comprise a status on a user interface device of the BAC level.

In another, more detailed feature of the invention, the method may further comprise, before step (d), repeating steps (a) through (c) for one or more additional drinking events to establish ranges of impairment or intoxication.

According to yet another aspect of the invention, there is provided a method for assessing drinking behavior to predict when the consumption of alcohol is likely to result in a feeling of being hungover, the method comprising the following steps: (a) obtaining a first objective transdermal alcohol response curve of a user for a first drinking event, wherein the first objective transdermal alcohol response curve is obtained using a transdermal alcohol sensor device; (b) querying the user about the user's subjective feelings about being hungover from the first drinking event; (c) correlating the user's subjective feelings of being hungover to the first objective transdermal alcohol response curve; (d) monitoring the user during a second drinking event to obtain a second objective transdermal alcohol response curve using the transdermal alcohol sensor device; and (e) providing a notification to the user, based on the second objective transdermal alcohol response curve from the second drinking event and a correlation between the user's subjective feelings of being hungover and the first objective transdermal alcohol response curve from the first drinking event, about a possible hangover for the second drinking event.

In another, more detailed feature of the invention, the correlating step may comprise correlating the user's subjective feelings of being hungover to an alcohol response rate derived from the transdermal alcohol response curve.

In another, more detailed feature of the invention, the correlating step may comprise correlating the user's subjective feelings of being hungover to an area under the transdermal alcohol response curve.

In another, more detailed feature of the invention, the querying step may be performed after the blood alcohol level of the user has returned to a baseline level.

In another, more detailed feature of the invention, the querying step may comprise providing the user with at least two options for a response.

In another, more detailed feature of the invention, the querying step may comprise providing the user with at least three options for a response.

In another, more detailed feature of the invention, the notification may comprise an alert or status on a user interface device.

According to a further aspect of the invention, there is provided a system for assessing drinking behavior, the system comprising: (a) a wearable transdermal alcohol sensor device; and (b) a user interface device in communication with the wearable transdermal sensor device, the user interface device being configured with an application to receive a transdermal alcohol measurement from the wearable transdermal alcohol sensor device corresponding to a first drinking event, to pose a query to a user about a subjective effect on the user of the first drinking event and to receive a response from the user to the query, to correlate the response of the user with the first transdermal alcohol measurement to obtain a correlating factor, to receive a second transdermal alcohol measurement of the user from the transdermal alcohol sensor device for a second drinking event, to use the correlating factor and the second transdermal alcohol measurement to predict the subjective effect on the user from the second drinking event, and to notify the user of the prediction.

In another, more detailed feature of the invention, the user interface device may be selected from the group consisting of a smartphone, tablet or PC.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. These drawings are not necessarily drawn to scale, and certain components may have undersized and/or oversized dimensions for purposes of explication. In the drawings wherein like reference numeral represent like parts.

DETAILED DESCRIPTION OF THE INVENTION

The present invention is directed at a method and system for assessing drinking behavior, wherein the method and system use a correlation between an objective transdermal alcohol measurement and a user's subjective feelings of the effects of alcohol (e.g., feeling intoxicated, feeling hungover) from a first drinking event to provide an alert or status, in real-time, for a second drinking event.

Figure 1:
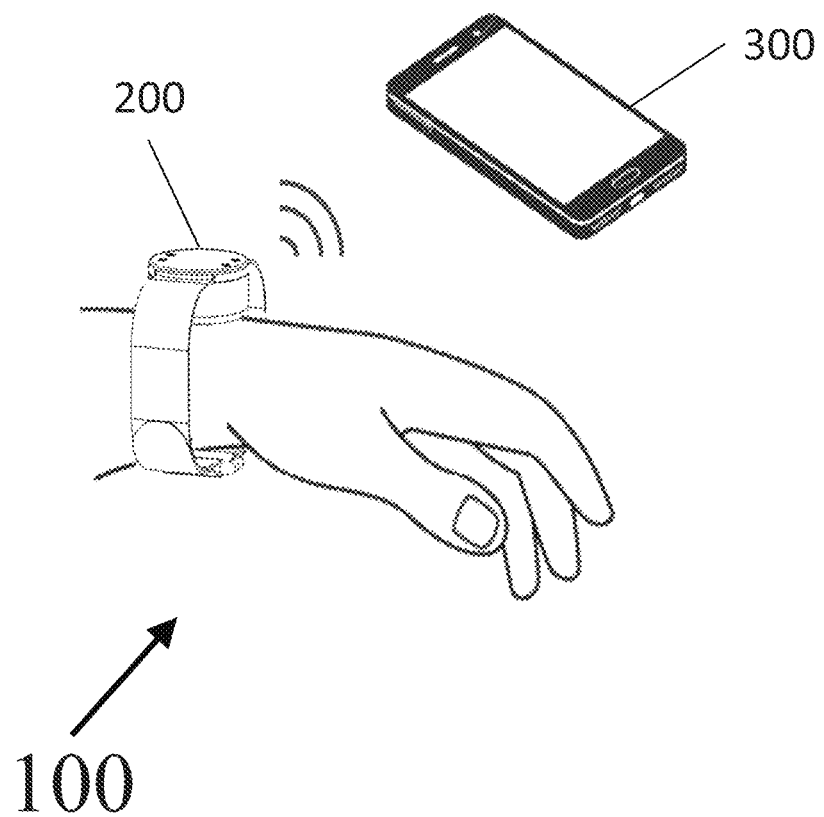
FIG. 1 is a perspective view of one embodiment of a system for the assessment of drinking behavior, the system being constructed according to the teachings of the present invention and including a wearable transdermal alcohol sensor device, which is shown worn on the wrist of a person.

Referring to FIG. 1, there is shown one embodiment of a system for the assessment of drinking behavior, the system being represented generally by reference numeral 100. System 100 may comprise a transdermal alcohol sensor device 200 and a user interface device 300, wherein transdermal alcohol sensor device 200 and user interface device 300 are capable of communicating with each other. User interface device 300 may comprise a smartphone, tablet, PC, or similar device. User interface device 300 may further comprise a software application to receive user input and to display output for performing the method described below for assessing a drinking behavior.

Transdermal alcohol sensor device 200 may be worn around the wrist of a user so that alcohol vapor diffusing through the skin of the user may diffuse to an alcohol sensing component contained inside transdermal alcohol sensor device 200. Alternatively, transdermal alcohol sensor device 200 may be secured at other locations on a user's body that provide transdermal alcohol sensor device 200 with access to the alcohol vapor diffusing through the skin of the user. Both transdermal alcohol sensor device 200 and user interface device 300 possess the capability to transmit and receive information using Bluetooth, Bluetooth Low Energy, or an equivalent wireless means of communication.

Figure 2:
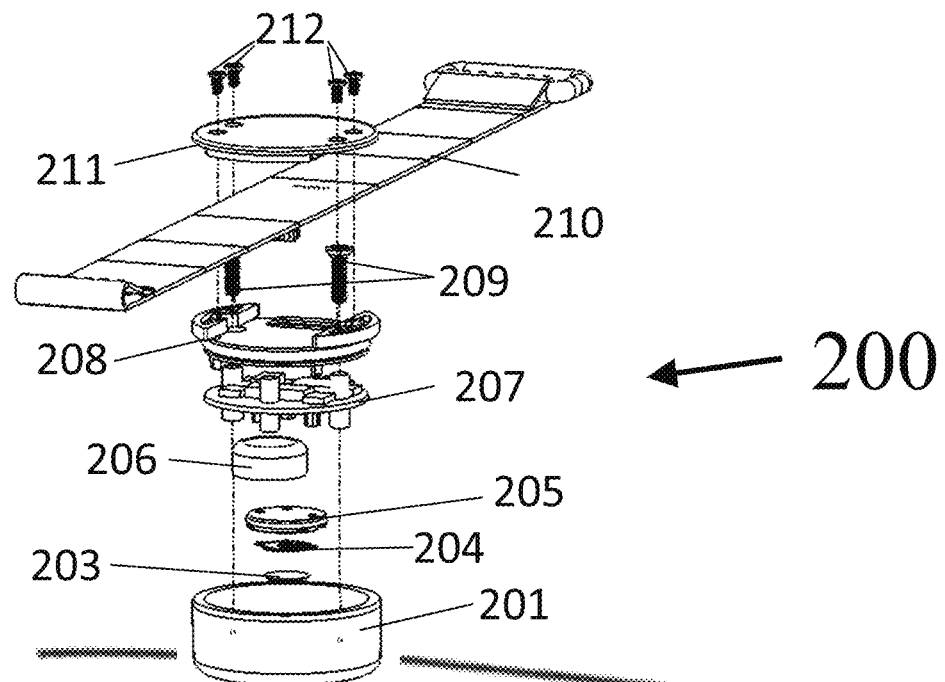
FIG. 2 is an enlarged exploded perspective view of the wearable transdermal alcohol sensor device shown in FIG. 1.
Figure 2:
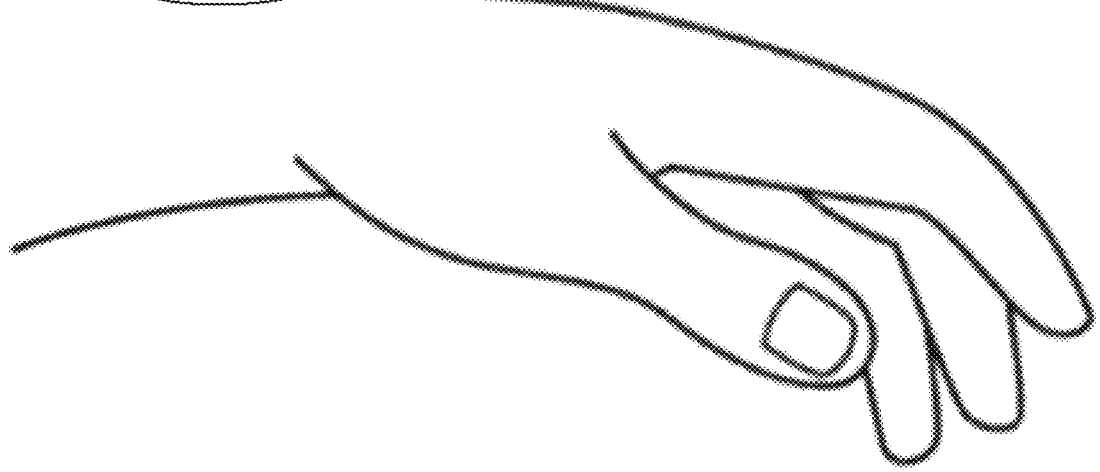
Figure 3:
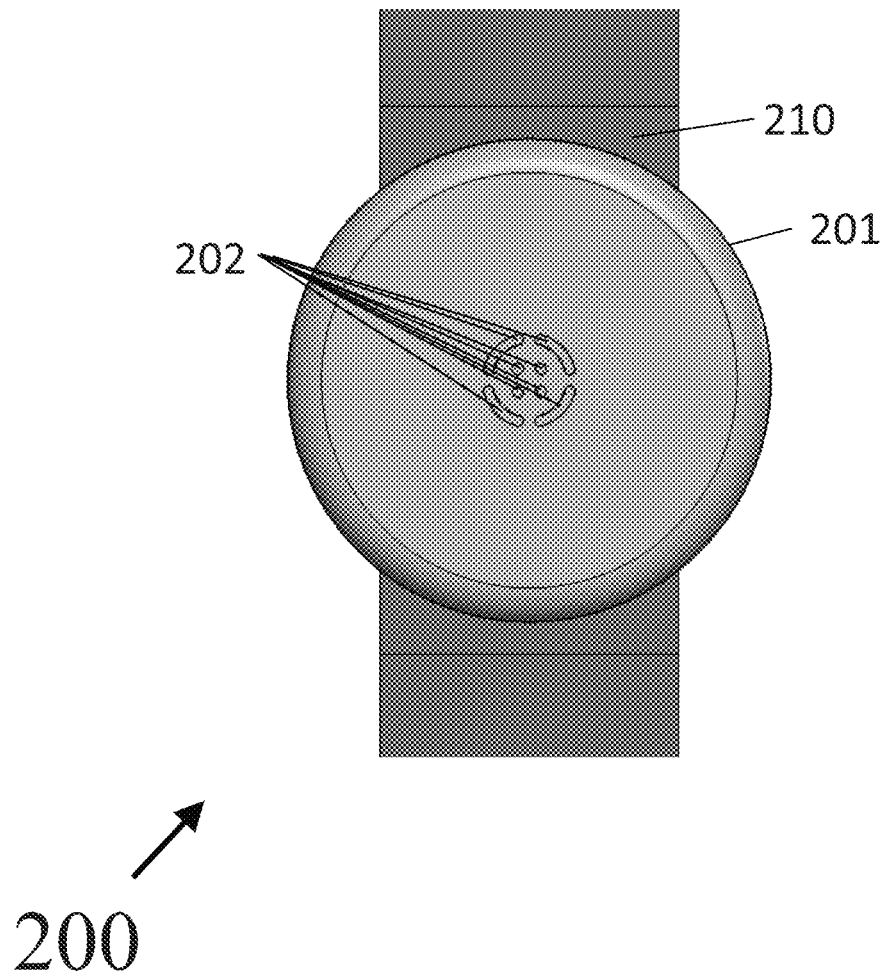
FIG. 3 is a fragmentary bottom view of the wearable transdermal alcohol sensor device shown in FIG. 2.

Referring now to FIG. 2, an exploded perspective view of transdermal alcohol sensor device 200 is shown. Device 200 may comprise a bottom housing 201 that may be placed in direct physical contact with the skin of a user. Bottom housing 201 may be provided with one or more access slots 202 on a bottom wall (see FIG. 3) that allow alcohol vapor diffusing through the skin of a user to also diffuse into the interior of bottom housing 201.

Device 200 may further comprise a gas permeable/liquid impermeable membrane 203 that may seal access slots 202 on the interior of bottom housing 201. Gas permeable/liquid impermeable membrane 203 may be sealed against the top surface of the bottom wall of bottom housing 201 using ultrasonic welding, heat-bonding, gasketing, or an equivalent means. Gas permeable/liquid impermeable membrane 203 comprises a membrane that is permeable to alcohol vapor, but impermeable to liquids. Examples of materials that may be used as gas permeable/liquid impermeable membrane 203 may include, but are not limited to, a silicone membrane, a silicone polycarbonate composite membrane, a liquid impermeable polytetrafluoroethylene (PTFE) membrane, a liquid impermeable polyvinylidene fluoride (PVDF) membrane, or any equivalent gas permeable/liquid impermeable membrane.

As alcohol vapor diffuses through the gas permeable/liquid impermeable membrane 203, the alcohol vapor may then be oxidized by an alcohol sensing element 204. Alcohol sensing element 204 may consist of or comprise the same or a substantially similar electrochemical alcohol sensor cell as is disclosed in U.S. Pat. No. 5,944,661, inventors Swette et al., which issued Aug. 31, 1999, and which is incorporated herein by reference in its entirety.

Device 200 may further comprise a sealing cap 205 to provide a sealed enclosure for alcohol sensing element 204 within bottom housing 201. Sealing cap 205 may further provide electrical connections (not shown) to the sensing, counter, and reference electrodes of alcohol sensing element 204 using gold pins sealed or molded within sealing cap 205, wherein the bottom of each gold pin is electrically-connected to one of the electrodes and the top of each gold pin may be accessed on a top side of sealing cap 205.

Device 200 may further comprise an electronics board 207, which, in turn, may comprise electrical contacts (not shown), such as gold pins, that are in electrical connection with each of the gold pins on the surface of sealing cap 205. Electronics board 207 may further comprise the same or a substantially similar potentiostatic control circuit as is used in U.S. Pat. No. 5,944,661 using said electrical connections to sensing, counter, and reference electrodes. Electronics board 207 may further comprise a microprocessor for supplying power to the potentiostatic circuit and for receiving and processing the signal output from the potentiostatic control circuit. Electronics board 207 may further comprise a wireless communication module (e.g., Texas Instruments™ CC2540 chip for Bluetooth low energy data transmission; Ublox Sara G-3 series chip for cellular transmission) so that information may be transmitted to and received from user interface device 300.

Device 200 may further comprise a battery 206 for supplying power to alcohol sensing element 204 and/or electronics board 207. Battery 206 may comprise a rechargeable or non-rechargeable coin cell battery.

Device 200 may further comprise a top housing 208, which may be secured against bottom housing 201 using one or more screws 209 to provide a sealed enclosure for battery 206, alcohol sensing element 204, electronics board 207, and the other internal components of device 200.

Device 200 may further comprise a wristband 210, which may be secured between top housing 208 and a strap retainer 211 using one or more screws 212.

System 100 may be utilized according to one or more of the methods described below.

According to one embodiment of the present invention, there is disclosed a method for assessing drinking behavior to predict when the consumption of alcohol is likely to result in a feeling of impairment or intoxication. Such a method may comprise the following steps: (a) determining a peak blood alcohol (BAC) level of a user for a first drinking event, wherein the peak BAC level is detected using a transdermal alcohol sensor device; (b) querying the user about the user's subjective feelings of impairment or intoxication relating to the first drinking event; (c) correlating the user's subjective feelings of impairment or intoxication relating to the first drinking event to the peak BAC level from the first drinking event to establish a correlating factor; (d) monitoring the BAC level of the user during a second drinking event using the transdermal alcohol sensor device; and (e) providing a notification to the user, based on the BAC level of the user during the second drinking event and the correlating factor derived from the first drinking event, about potential for feelings of impairment or intoxication from the second drinking event.

Figure 4:
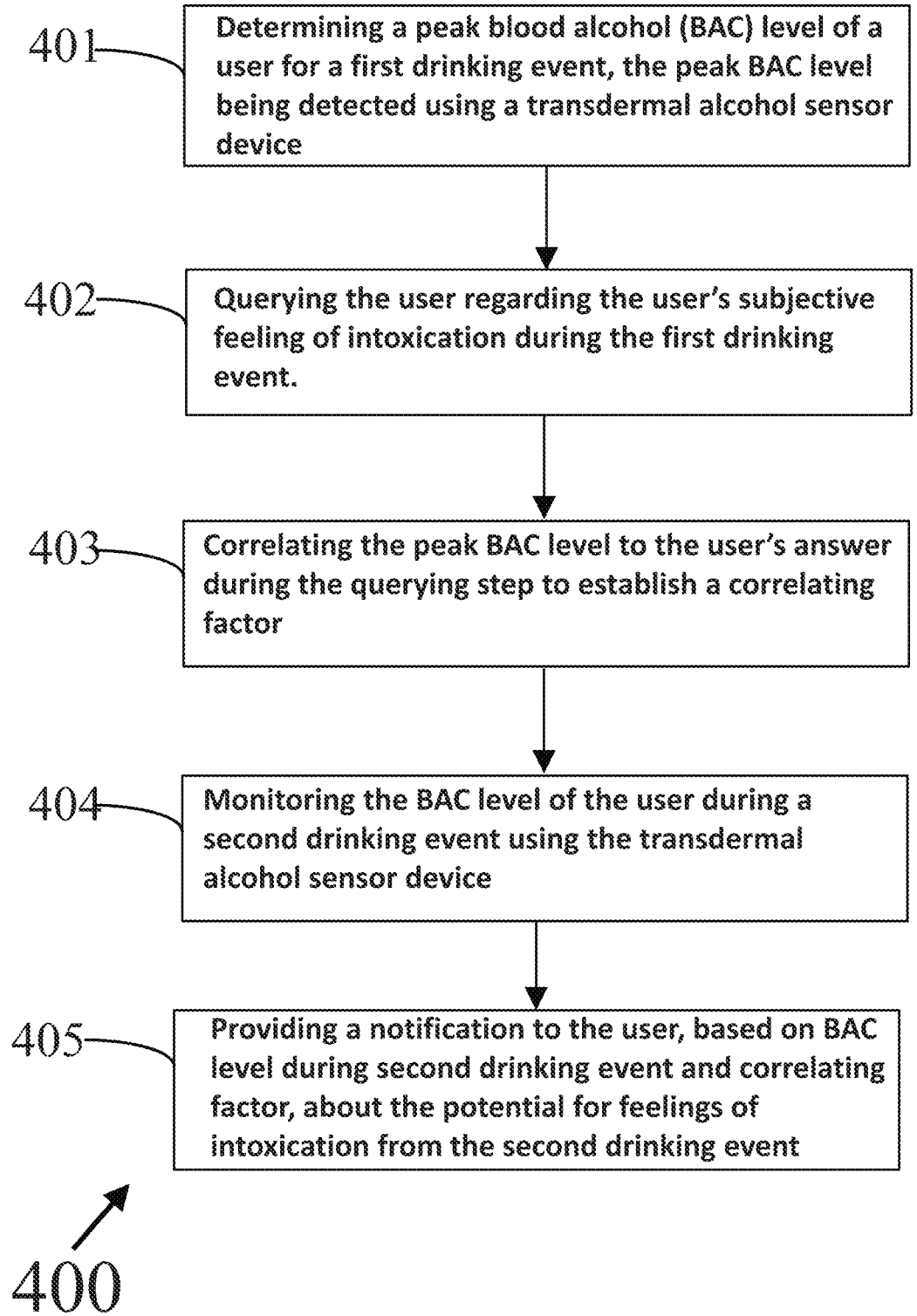
FIG. 4 is a flowchart illustrating one embodiment of a method for the assessment of intoxication according to the teachings of the present invention.
Figure 5:
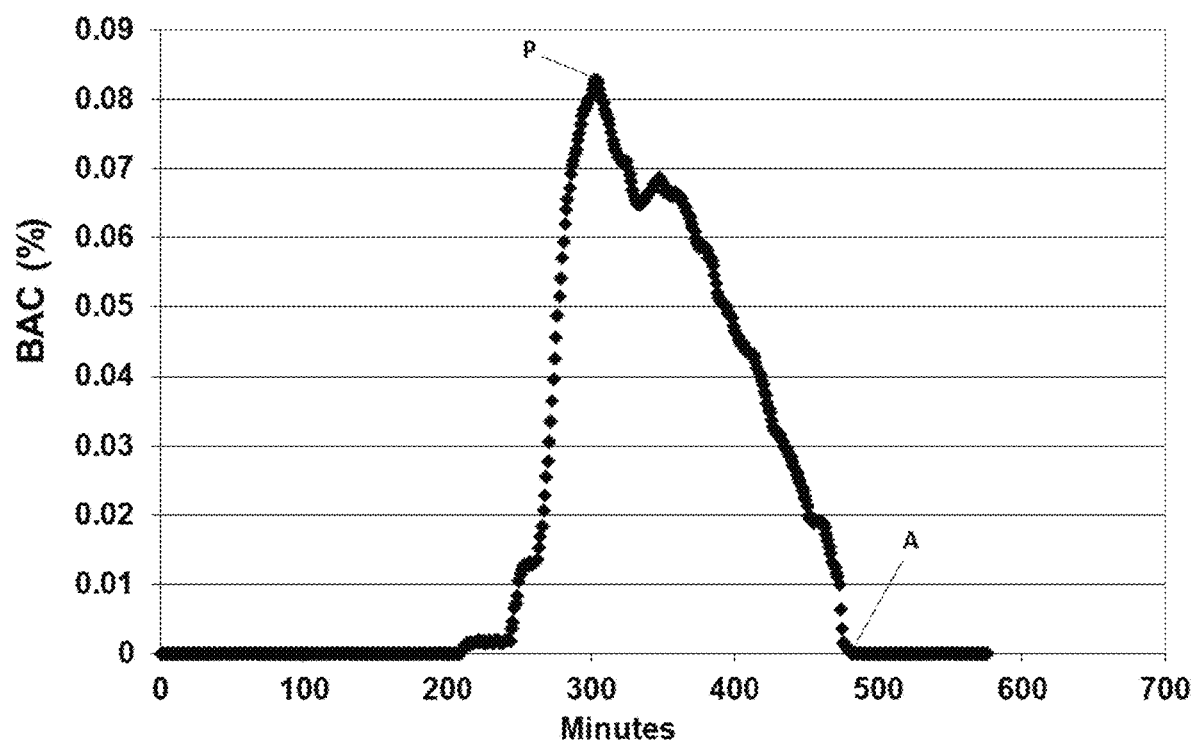
FIG. 5 is a graph depicting a prophetic transdermal alcohol response curve of the type that may be obtained using the device of FIG. 1.

Referring now to FIG. 4, there is shown a flowchart, illustrating the above-described method. As can be seen, the method is represented generally by reference numeral 400. Method 400 may begin with a determining step 401. Determining step 401, in turn, may comprise obtaining from a user, using a wearable transdermal alcohol device like device 200, an alcohol response curve resulting from a first drinking event, and analyzing the alcohol response curve to find the peak blood alcohol content level from the first drinking event. For example, FIG. 5 illustrates a prophetic transdermal alcohol response curve wherein the measured transdermal alcohol vapor is correlated to % BAC. For purposes of this disclosure, a drinking event may be defined as a rise in the % BAC of 0.02% or greater. Analyzing step 401 preferably determines the peak % BAC value (i.e., Point P) once the detected % BAC has returned to background (i.e., Point A).

Figure 6:
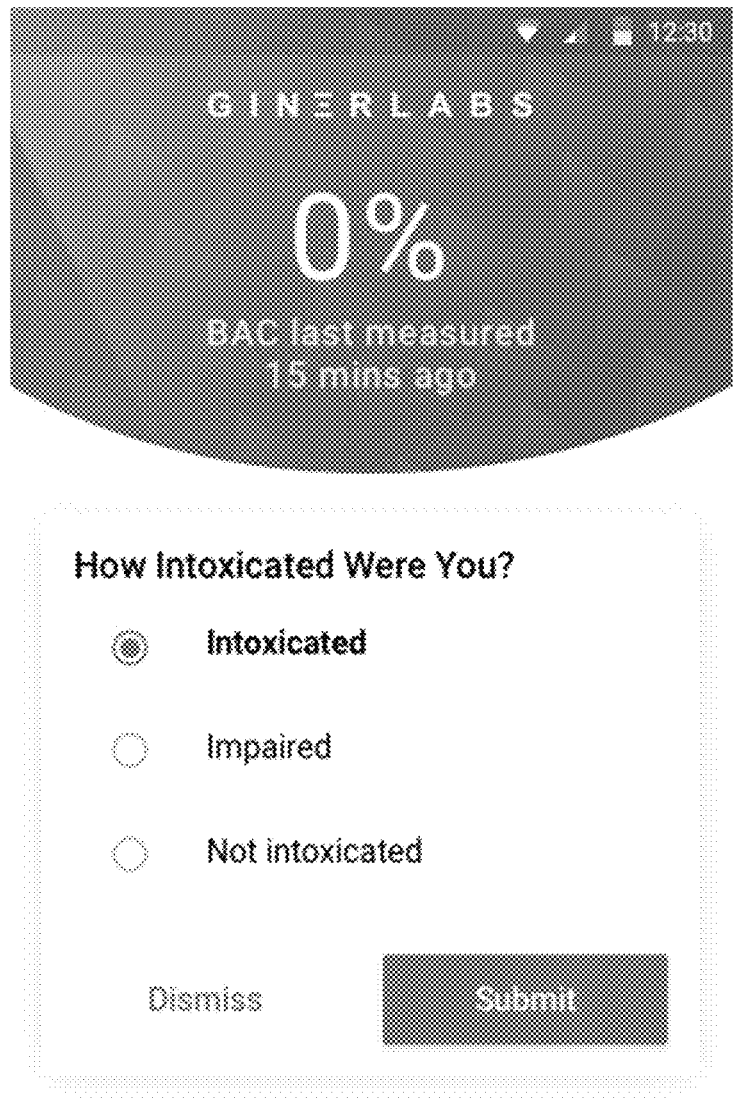
FIG. 6 is a pictorial representation of a display of a user interface application according to the teachings of the present invention, the user interface application querying a user about the user's previous feeling of intoxication.

Referring back to FIG. 4, method 400 may then continue with a querying step 402. Preferably, querying step 402 is performed after the transdermal alcohol sensor device has detected that the user's BAC level has returned to background or baseline (i.e., at Point A or a time after Point A while the subject is still measuring 0.00% BAC). During querying step 402, an application on an interface device will ask the user a self-assessing question about the user's subjective feelings of intoxication during the first drinking event. The user will then be provided with at least two options for answering the question, wherein the at least two options may offer descriptions of different levels of intoxication. For example, FIG. 6 provides one embodiment of the query, wherein the application queries the user on how intoxicated the user felt, and offers three options for a response: (1) "Intoxicated," (2) "Impaired," and (3) "Not Intoxicated."

Referring back to FIG. 4, method 400 may then continue with a correlating step 403. Correlating step 403 may relate the answer provided in querying step 402 to the peak BAC level determined during analyzing step 401. For example, referring again to the transdermal alcohol response curve in FIG. 5, if the user answered "Impaired" during querying step 402, that response would be correlated to the peak BAC level measured during analyzing step 401 (i.e., Point P or 0.085% BAC). In this manner, a correlating factor or standard may be established that "Impaired" correlates with the peak BAC level.

Referring back to FIG. 4, method 400 may then continue with a monitoring step 404. During monitoring step 404, the BAC of the user may be monitored using the transdermal alcohol sensor device.

Figure 7:
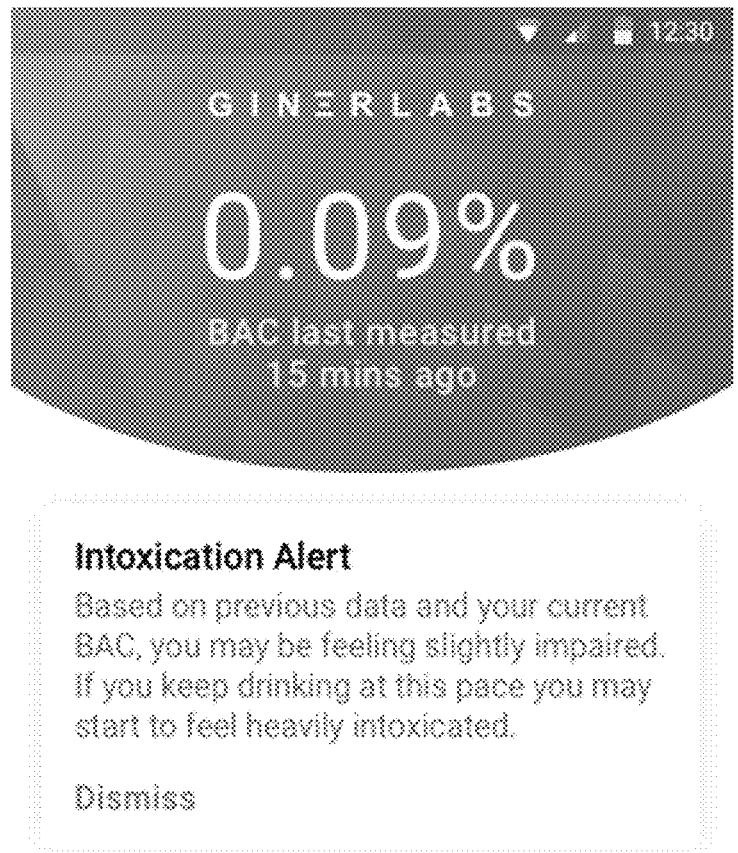
FIG. 7 is a pictorial representation of a display of the user interface application of FIG. 6, the user interface application providing an intoxication alert.

Method 400 may further comprise a notification step 405, wherein a notification to the user about a second drinking event may be based on the BAC level of the user during the second drinking event and the correlating factor derived from the correlation between the user's subjective feelings of intoxication relating to the first drinking event and the peak BAC level from the first drinking event. For example, notification step 405 may comprise providing an intoxication alert to the user during the second drinking event if the transdermal alcohol sensor device detects a BAC that meets or exceeds the correlating factor obtained in correlating step 403. For example, referring now to FIG. 7, there is shown one embodiment of an intoxication alert that appears on the user interface device when the user reaches 0.09% BAC. In this particular example, the correlation would have previously established a standard that the user felt "Impaired" at a level of 0.09% BAC, and the alert would appear on the user interface device once the user reaches a 0.09% BAC level as measured by the transdermal alcohol sensor device. Even if the BAC from the second drinking event has not met or exceeded the correlation factor, the user interface device may display some sort of textual notification of status.

Figure 8A:
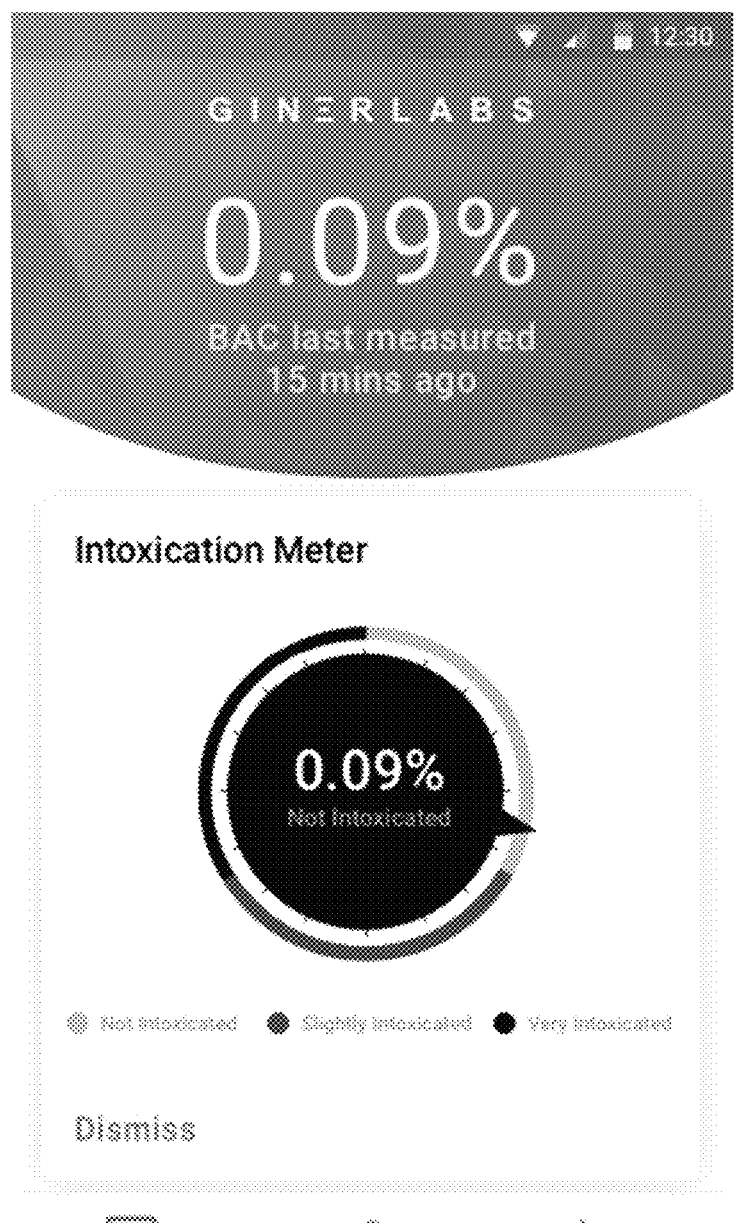
FIGS. 8(a) and 8(b) are alternative displays of the user interface application of FIG. 6.
Figure 8B:
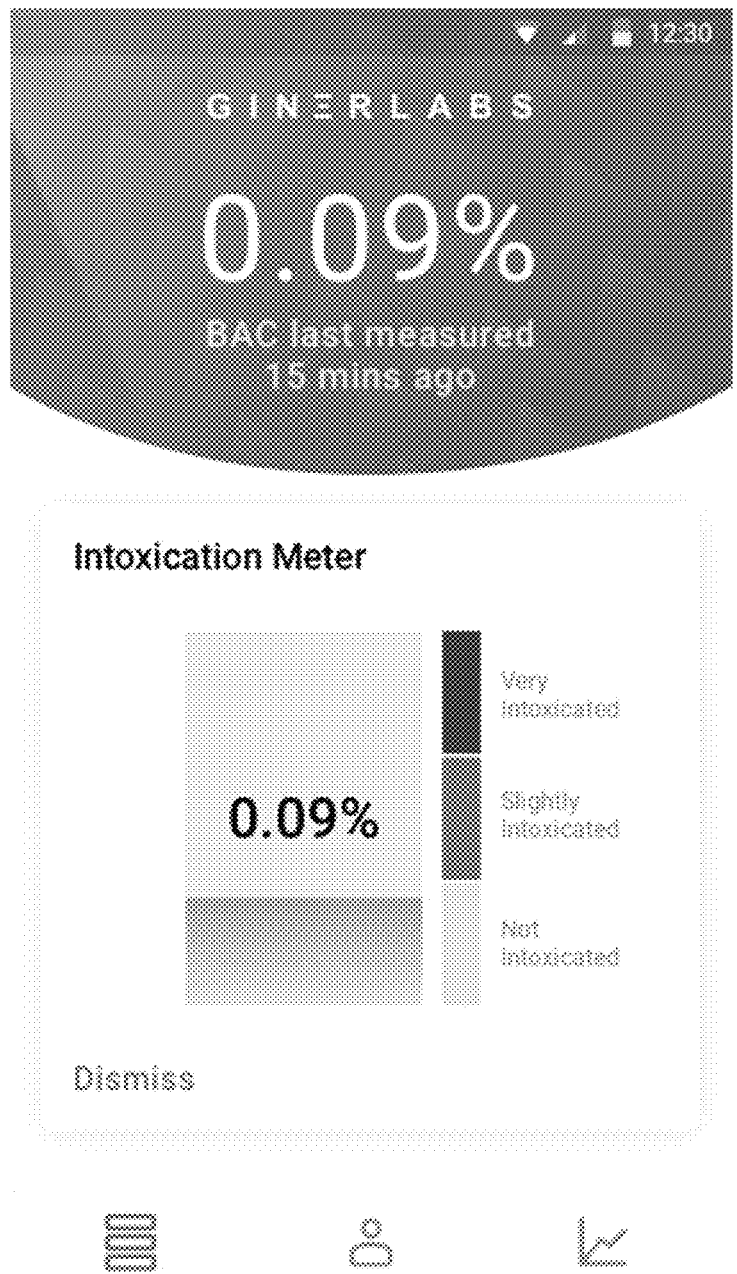

In an alternative embodiment, notification step 405 may comprise displaying a status level in graphical form. For instance, the user interface may display a dial (see FIG. 8(*a*)) or bar graph (see FIG. 8(*b*)) with regions for one or more levels of intoxication. As the measured % BAC from the transdermal alcohol device begins to rise, the bar in the display will move up (or a dial may move left or right) and approach a threshold or cross a threshold into a different level of intoxication. As the bar or dial moves into another region of intoxication, a change of color or an indicator light may alert the user to the change in intoxication level.

Notification step 405 may further comprise incorporating predictive statements. For instance, based on the rate at which the user is drinking, the device would calculate that the user is on a pace to reach a % BAC in which the user would reach a new intoxication level. Referring again to FIG. 7, the second sentence indicates that the current rate of drinking would cause the user to go from "Impaired" to "Heavily Intoxicated."

In a further embodiment of the present invention, the steps of the method may be repeated during subsequent drinking events to establish ranges of intoxication. These steps may be repeated for each drinking event measured by the transdermal alcohol sensor device. The repeated steps may then be used to establish multiple correlation standards that would then be collated into intoxication intervals. For instance, based on the correlations, a particular user may find that a rate of 0.00-0.060% BAC correlates to "Not Intoxicated," 0.061-0.110% BAC correlates to "Impaired," and greater than 0.110% BAC correlates to "Intoxicated." The intoxication alerts or drinking status graphical depictions may then update as these ranges are updated with each subsequent drinking event.

In an alternative embodiment of the method, determining step 401 may comprise setting one or more pre-determined BAC levels. As a user reaches the one or more pre-determined BAC level(s) as measured by the transdermal alcohol sensor device, the method may proceed to the querying step. In other words, instead of performing the querying step after the drinking event has ended and the BAC level returns to point A, the querying step may occur at the same time that a pre-determined BAC level is measured by the transdermal alcohol sensor device. For example, as soon as the transdermal alcohol sensor device detects 0.05% BAC, the querying step may occur. In this embodiment, there may be multiple pre-determined BAC levels (e.g., 0.05, 0.08, 0.01% BAC) at which times the querying step is performed.

According to another embodiment of the invention, there is provided a method for assessing drinking behavior to predict when the consumption of alcohol is likely to result in a feeling of being hungover. Such a method may comprise the following steps: (a) obtaining a first objective transdermal alcohol response curve of a user for a first drinking event, wherein the first objective transdermal alcohol response curve is obtained using a transdermal alcohol sensor device; (b) querying the user about the user's subjective feelings about being hungover from the first drinking event, (c) correlating the user's subjective feelings of being hungover to the first objective transdermal alcohol response curve, (d) monitoring the user during a second drinking event to obtain a second objective transdermal alcohol response curve using the transdermal alcohol sensor device, and (e) providing a notification to the user, based on the second objective transdermal alcohol response curve from the second drinking event and a correlation between the user's subjective feelings of being hungover and the first objective transdermal alcohol response curve from the first drinking event, about a possible hangover for the second drinking event.

Figure 9:
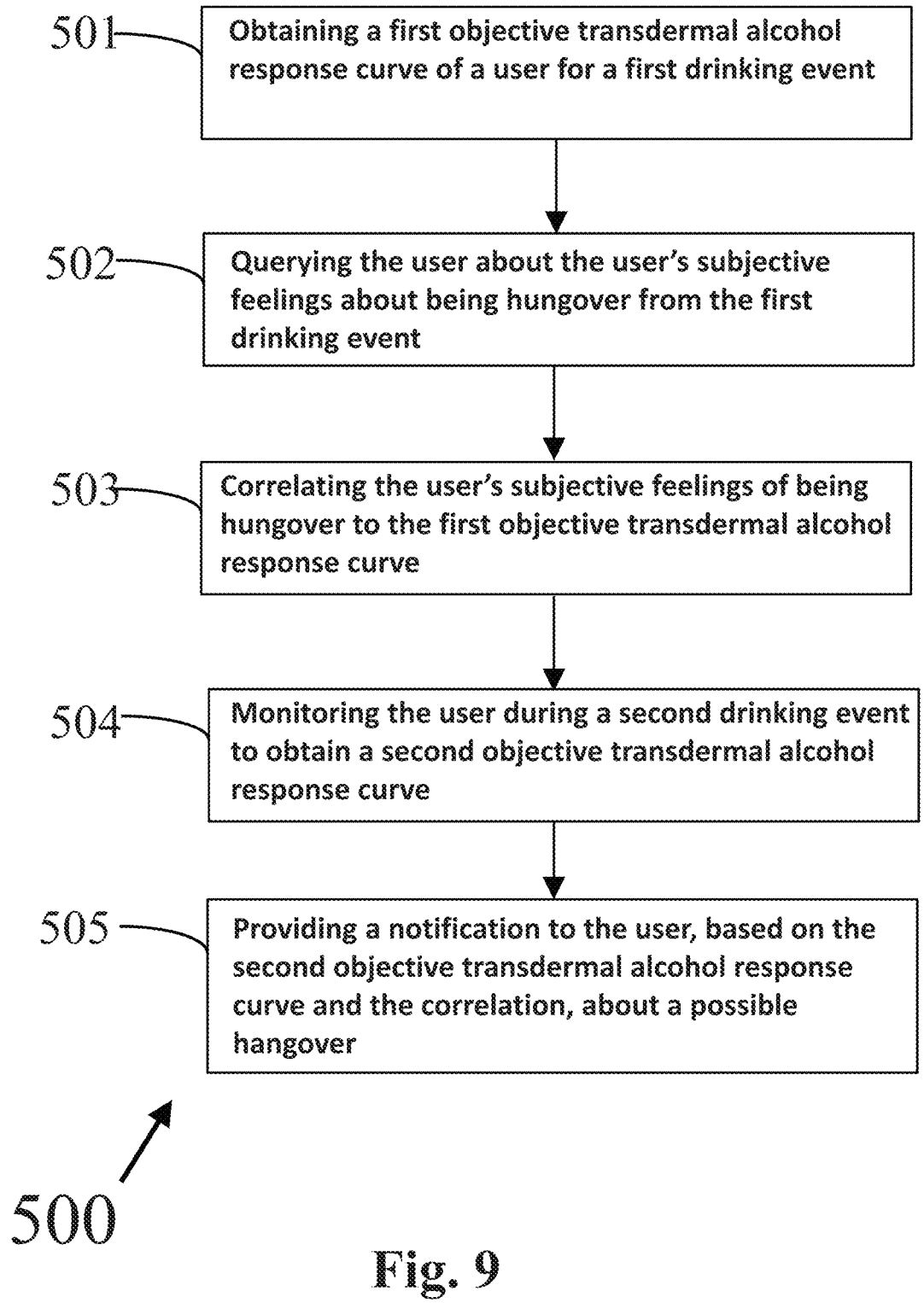
FIG. 9 is a flowchart illustrating one embodiment of a method for the assessment of a potential hangover according to the teachings of the present invention.

Referring now to FIG. 9, method 500 may begin with a determining step 401. Determining step 401, in turn, may comprise obtaining from a user, using a wearable transdermal alcohol device like device 200, an alcohol response curve resulting from a first drinking event, and analyzing the alcohol response curve to calculate the alcohol response rate between two selected points on the curve. For example, FIG.

10 illustrates a prophetic transdermal alcohol response curve wherein the measured transdermal alcohol vapor is correlated to % BAC. The alcohol response rate may be calculated from a point at the beginning of the alcohol response (e.g. Point A) to the peak BAC point (e.g. Point P) on the alcohol response curve. Alternatively, the alcohol response rate may be calculated from a point at the beginning of drinking (e.g. Point A) to a point where response is still rising (e.g. Point B). The alcohol response rate may be expressed in % BAC/min, % BAC/hr, mg/(dL-min), or mg/(dL-hr). In an alternative embodiment, the analyzing step may comprise using an alcohol response curve generated by a wearable transdermal alcohol device to calculate the area under the curve between two points. For instance, the area under the curve from a point at the beginning of drinking (e.g. Point A) to the peak BAC point (e.g. Point P) on the alcohol response curve may be calculated. Alternatively, the area under the curve may be calculated from a point at the beginning of drinking (e.g. Point A) to a point where the alcohol response is still rising (e.g. Point B).

Figure 10:
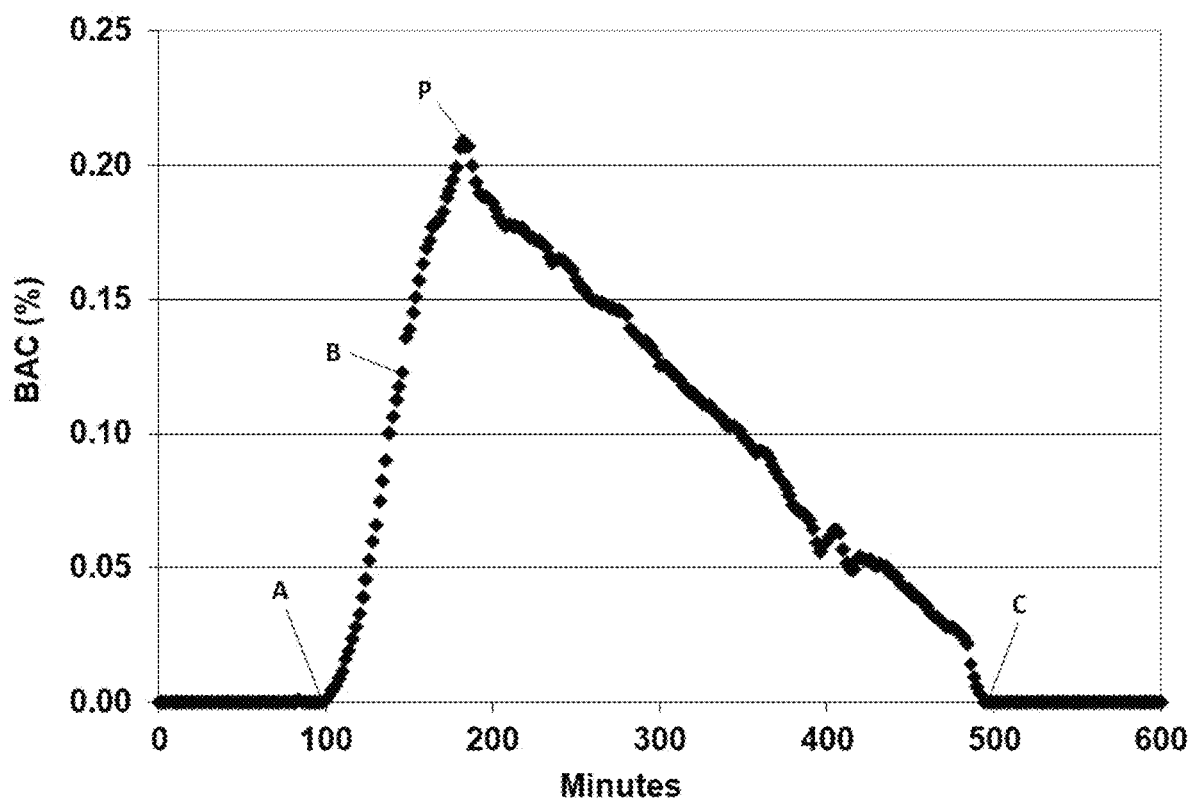
FIG. 10 is a graph depicting a prophetic transdermal alcohol response curve of the type that may be obtained using the device of FIG. 1.
Figure 11:
FIG. 11 is a pictorial representation of a user interface application according to the teachings of the present invention, the user interface application querying a user about the user's feelings about being hungover.
Figure 11:
Figure 11:

Method 500 may further comprise a querying step 502. Querying step 502 may comprise asking the user a question about the user's subjective feelings related to being hungover after the first drinking event has taken place. When the transdermal alcohol sensor device detects that the person is back at background or baseline BAC level (see, e.g., Point C in FIG. 10), the application on the user interface device may ask if the user feels hungover and may offer two or more answers from a pre-determined set of two or more answers indicating different hangover levels. For example, FIG. 11 illustrates one embodiment of a display from the user interface device wherein the user is queried on how hungover the user feels and offers three options for a user response: (1) "Very Hungover," (2) "A Little Hungover," and (3) "Not Hungover."

Method 500 may further comprise a correlating step 503. Correlating step 503 may comprise correlating the alcohol response rate or area under the curve calculated during the determining step 501 to the answer provided by the user during querying step 502. For example, in the case where the user selects the "Very Hungover" answer, the alcohol response rate or the area under the curve values calculated during the analyzing step may be assigned the "Very Hungover" level.

Referring back to FIG. 9, method 500 may then continue with a monitoring step 504. During monitoring step 504, a second objective transdermal alcohol response curve of the user may be obtained using the transdermal alcohol sensor device.

Figure 12:
FIG. 12 is a pictorial representation of a display of the user interface application of FIG. 11, the user interface application providing a hangover alert.
Figure 12:

Method 500 may further comprise a notification step 505, wherein a notification to the user about a second drinking event may be based on the second objective transdermal alcohol response curve of the user during the second drinking event and the correlation between the user's subjective feelings of being hungover from the first drinking event and the first objective transdermal alcohol response curve. For example, notification step 505 may comprise providing a hangover alert or status to the user during the second drinking event if the transdermal alcohol sensor device detects an alcohol response rate or area under the alcohol response curve that meets or exceeds the correlation obtained in correlating step 503. For instance, if the correlation from the first drinking event establishes that an alcohol response rate of 0.04% BAC/hr or greater correlates to the particular user having a hangover, if the subsequent drinking event has an alcohol response rate of 0.05% BAC/hr, then an alert will be displayed. FIG. 12 illustrates one embodiment of a hangover alert that may appear in the application of the user interface device. Alternatively, the device or smartphone application may display a continuous drinking status wherein the status changes according to the change in the alcohol response rate. For instance, during the initial alcohol response, the status may display "No Hangover," but, as the alcohol response rate rises above 0.04% BAC/hr, for example, then the drinking status may change to "Hangover Rate." In a further embodiment, the device or smartphone application may display instructions, such as "Drink More Water" or "Eat Some Food," which may assist the user in slowing down the user's drinking rate.

In an alternative embodiment, notification step 505 may comprise displaying a status level in graphical form. For instance, the user interface may display a dial or bar graph with regions for hangover rate levels. As the measured % BAC from the transdermal alcohol device begins to rise, the bar in the display will move up (or a dial may move left or right) and cross the threshold into a different hangover level. As the bar or dial moves into another hangover level, a change of color or an indicator light may alert the user to the change in hangover level.

In a further embodiment of the present invention, the steps of the method may be repeated each time the transdermal alcohol sensor device detects a drinking event. The method repetitions may be used to establish multiple correlation factors that would then be collated into hangover level intervals. For instance, based on the correlations, a particular user may find that a rate of 0.00-0.02% BAC/hr correlates to "Not Hungover," 0.02-0.04% BAC correlates to "A Little Hungover," and greater than 0.04% BAC/hr correlates to "Very Hungover." Similarly, intervals correlating the area under the curve to the hangover levels may be established from multiple drinking events. These intervals may be updated for each subsequent drinking event detected by the transdermal alcohol sensor device.

As can be appreciated, unless expressly prohibited herein or otherwise incompatible therewith, elements of the method for assessing drinking behavior to predict when the consumption of alcohol is likely to result in a feeling of impairment or intoxication may be combined with and/or exchanged with elements of the method for assessing drinking behavior to predict when the consumption of alcohol is likely to result in a feeling of being hungover.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A system for assessing alcohol response, the system comprising:
 a wearable transdermal sensor device that measures alcohol vapor diffusing through skin; and
 a user interface device in communication with the wearable transdermal sensor device, wherein the user interface device includes one or more software applications that cause the user interface device to perform operations comprising:
  receive, from the wearable transdermal sensor device, a first transdermal alcohol measurement of alcohol vapor diffusing through skin of a user during a first drinking event;

generate and display, on the user interface device, a query about a subjective effect on the user of the first drinking event;
receive, via the user interface device, a response to the displayed query;
generate a user-specific correlating factor specific to the user by correlating the received response to the query and the first transdermal alcohol measurement for the first drinking event;
during a second drinking event:
receive, from the wearable transdermal sensor device, a second transdermal alcohol measurement of alcohol vapor diffusing through the skin of the user;
generate a subjective-effect prediction for the user based the generated user-specific correlating factor and the second transdermal alcohol measurement; and
generate and display, on the user interface device, an alert based on the subjective-effect prediction for the user.

2. The system of claim 1, wherein the wearable transdermal sensor device is configured to be worn on a wrist of the user.

3. The system of claim 2, wherein the wearable transdermal sensor device comprises:
a bottom housing configured to be in physical contact with the wrist;
one or more access slots, on a bottom wall of the bottom housing, through which the alcohol vapor flows;
a top housing; and
a wristband to secure the wearable transdermal sensor device to the wrist.

4. The system of claim 1, wherein the alert includes displaying a status level.

5. The system of claim 4, wherein the status level is displayed in a graphical form that is one of a dial or a bar graph with regions for one or more levels of intoxication.

6. The system of claim 1, wherein the user interface device is one of a smartphone, a tablet, or a personal computer.

7. A system for assessing alcohol response, the system comprising:
a wearable transdermal sensor device that measures alcohol vapor diffusing through skin; and
a computing device, in communication with the wearable transdermal sensor device, wherein the computing device includes a display and one or more software applications that cause the computing device to perform operations comprising:
receive, from the wearable transdermal sensor device, first transdermal alcohol measurements of alcohol vapor diffusing through skin of a user during a first drinking event;
based on the first transdermal alcohol measurements, determining a peak blood alcohol level for the first drinking event;
generate a query about a subjective evaluation of at least one of impairment or intoxication relating to the first drinking event;
receive, via the computing device, a response to the query;
generate a user-specific correlating factor specific to the user by correlating the received response to the query and the peak blood alcohol level from the first drinking event;
receive, from the wearable transdermal sensor device, second transdermal alcohol measurements of alcohol vapor diffusing through the skin of the user during a second drinking event; and
during the second drinking event and based on predictions associated with the second transdermal alcohol measurements of the user during the second drinking event and the user-specific correlating factor generated from the first drinking event, generate a notification about at least one of potential impairment or potential intoxication from the second drinking event.

8. The system of claim 7, wherein the operations further comprise:
determine, from the first transdermal alcohol measurements, an alcohol response rate; and
wherein the user-specific correlating factor is based on the alcohol response rate.

9. The system of claim 7, wherein the operations further comprise:
determine, from the first transdermal alcohol measurements, an area under the curve of a transdermal alcohol response curve formed from the first transdermal alcohol measurements; and
wherein the user-specific correlating factor is based on the area under the curve.

10. The system of claim 7, wherein the notification is includes displaying a status level.

11. The system of claim 7, wherein the operations further comprise:
receive third transdermal alcohol measurements after the first drinking event;
based on the third transdermal alcohol measurements, determine that a blood alcohol level of the user has returned to a baseline level; and
wherein the query is generated after the blood alcohol level has returned to the baseline level.

12. The system of claim 7, wherein the query is displayed with at least two options for responding to the query.

13. The system of claim 7, wherein the computing device is one of a smartphone, a tablet, or a personal computer.

14. A system for assessing alcohol response, the system comprising:
a wearable transdermal sensor device that measures alcohol vapor diffusing through skin; and
a computing device, in communication with the wearable transdermal sensor device, wherein the computing device includes a display and one or more software applications that cause the computing device to perform operations comprising:
receive, from the wearable transdermal sensor device, a first objective transdermal alcohol response curve based on measurements of alcohol vapor diffusing through skin of a user during a first drinking event;
generate a query about a subjective hangover response from the first drinking event;
receive, via the computing device, a response to the query;
generate a user-specific correlating factor specific to the user by correlating the received response to the query and the first objective transdermal alcohol response curve;
during a second drinking event:
receive, from the wearable transdermal sensor device, a second objective transdermal alcohol response curve based on measurements of alcohol vapor diffusing through the skin of the user during the second drinking event;

generate a predicted hangover response based on the user-specific correlating factor and the second objective transdermal alcohol response curve; and generate an alert, via the computing device, based on the predicted hangover response.

15. The system of claim 14, wherein the operations further comprise:

receive third transdermal alcohol measurements after the first drinking event;

based on the third transdermal alcohol measurements, determine that a blood alcohol level of the user has returned to a baseline level; and wherein the query is generated after the blood alcohol level has returned to the baseline level.

16. The system of claim 14, wherein the operations further comprise:

determine, from the first transdermal alcohol response curve, an alcohol response rate; and wherein the user-specific correlating factor is based on the alcohol response rate.

17. The system of claim 14, wherein the operations further comprise:

determine, from the first transdermal alcohol response curve, an area under the first transdermal alcohol response curve; and wherein the user-specific correlating factor is based on the area under the curve.

18. The system of claim 14, wherein the alert includes displaying a status level in a graphical form that is one of a dial or a bar graph with regions for one or more levels of intoxication.

19. The system of claim 14, wherein the wearable transdermal sensor device comprises:

a bottom housing configured to be in physical contact with a wrist;

one or more access slots, on a bottom wall of the bottom housing, through which the alcohol vapor flows;

a top housing; and a wristband to secure the wearable transdermal sensor device to the wrist.

20. The system of claim 14, wherein the computing device is one of a smartphone, a tablet, or a personal computer.

\* \* \* \* \*